(12) United States Patent
Ahmed et al.

(10) Patent No.: US 8,110,623 B2
(45) Date of Patent: Feb. 7, 2012

(54) HOT MELT PRESSURE SENSITIVE ADHESIVE COMPOSITION THAT INCLUDES VEGETABLE WAX AND ARTICLES INCLUDING THE SAME

(75) Inventors: Sharf U. Ahmed, Woodbury, MN (US); Steven R. Vaughan, Chisago Lakes Township, MN (US); Vitaly Rogachevsky, Woodbury, MN (US); Beth M. Eichler-Johnson, St. Paul, MN (US)

(73) Assignee: H.B. Fuller Company, St. Paul, MN (US)

( * ) Notice: Subject to any disclaimer, the term of this patent is extended or adjusted under 35 U.S.C. 154(b) by 849 days.

(21) Appl. No.: 11/862,475

(22) Filed: Sep. 27, 2007

(65) Prior Publication Data

US 2008/0076860 A1    Mar. 27, 2008

Related U.S. Application Data

(60) Provisional application No. 60/847,786, filed on Sep. 27, 2006.

(51) Int. Cl.
    *C08L 91/06*    (2006.01)

(52) U.S. Cl. ........ 524/275; 524/505; 524/272; 524/274; 156/327; 428/35.7; 428/511; 428/513

(58) Field of Classification Search .......... 524/505
    See application file for complete search history.

(56) References Cited

U.S. PATENT DOCUMENTS

| | | | |
|---|---|---|---|
| 4,010,130 A | 3/1977 | Matsuo et al. | |
| 4,081,282 A | 3/1978 | Merrill et al. | |
| 4,197,349 A * | 4/1980 | Walser | 428/378 |
| 4,419,494 A | 12/1983 | Puletti et al. | |
| 5,120,781 A | 6/1992 | Johnson, Jr. | |
| 5,149,741 A | 9/1992 | Alper et al. | |
| 5,177,133 A | 1/1993 | Peck et al. | |
| 5,262,479 A | 11/1993 | Tobing | |
| 5,322,876 A | 6/1994 | Sasaki et al. | |
| 5,705,551 A | 1/1998 | Sasaki et al. | |
| 6,143,818 A | 11/2000 | Wang et al. | |
| 6,166,142 A * | 12/2000 | Zhang et al. | 525/201 |
| 6,458,877 B1 * | 10/2002 | Ahmed et al. | 524/275 |
| 6,653,385 B2 | 11/2003 | Wang et al. | |
| 6,664,309 B2 | 12/2003 | Svenningsen et al. | |
| 6,984,680 B2 | 1/2006 | Quinn | |
| 7,059,760 B2 | 6/2006 | Mehta et al. | |
| 7,067,585 B2 | 6/2006 | Wang et al. | |
| 2002/0115744 A1 | 8/2002 | Svenningsen et al. | |
| 2002/0146526 A1 * | 10/2002 | Haner et al. | 428/35.7 |
| 2002/0161085 A1 | 10/2002 | Gibes et al. | |
| 2003/0096896 A1 | 5/2003 | Wang et al. | |
| 2003/0105259 A1 | 6/2003 | Heemann et al. | |
| 2003/0168165 A1 | 9/2003 | Hatfield | |
| 2003/0229168 A1 | 12/2003 | Borsinger et al. | |
| 2004/0081795 A1 | 4/2004 | Wang et al. | |
| 2004/0115456 A1 | 6/2004 | Kanderski et al. | |
| 2004/0119198 A1 | 6/2004 | Alper et al. | |
| 2004/0127614 A1 | 7/2004 | Jiang et al. | |
| 2004/0196734 A1 | 10/2004 | Mehta et al. | |
| 2005/0256254 A1 | 11/2005 | Luhmann et al. | |
| 2006/0014901 A1 | 1/2006 | Hassan et al. | |
| 2006/0093764 A1 | 5/2006 | Mehta et al. | |
| 2006/0142447 A1 | 6/2006 | Hatfield | |
| 2006/0199897 A1 | 9/2006 | Karjala et al. | |

FOREIGN PATENT DOCUMENTS

| | | |
|---|---|---|
| EP | 0 525 251 | 2/1993 |
| EP | 0 557 573 A2 | 9/1993 |
| EP | 1 013 291 | 6/2000 |
| EP | 1 342 765 | 9/2003 |
| WO | WO97/33921 | 9/1997 |
| WO | WO99/57201 | 11/1999 |

* cited by examiner

*Primary Examiner* — Doris Lee
(74) *Attorney, Agent, or Firm* — Allison Johnson; Kirsten Stone

(57) ABSTRACT

A hot melt pressure-sensitive adhesive composition that includes thermoplastic polymer, tackifying agent, plasticizer oil, and from at least 5% by weight to about 25% by weight vegetable wax.

30 Claims, No Drawings

HOT MELT PRESSURE SENSITIVE ADHESIVE COMPOSITION THAT INCLUDES VEGETABLE WAX AND ARTICLES INCLUDING THE SAME

CROSS REFERENCE TO RELATED APPLICATIONS

This application claims the benefit of U.S. Provisional Application No. 60/847,786, filed Sep. 27, 2006, which is incorporated herein.

BACKGROUND

Hot melt adhesive compositions are used in a variety of applications that require bonding two substrates together including, e.g., packaging applications (e.g., corrugated board and cardboard), bookbinding and footwear manufacturing. A hot melt adhesive composition is generally applied in a molten state and forms a bond as it cools and solidifies. The time required for a hot melt adhesive to cool to the point where it has enough strength to form a bond is referred to as the "set speed." Set speed is an important parameter in applications that require high speed processing operations such as packaging and book binding operations. For many packaging applications, the bond needs to form rapidly or the resulting package will be poorly sealed or even unsealed.

Waxes such as paraffin waxes, polyethylene waxes, microcrystalline waxes and Fischer-Tropsch waxes are added to hot melt compositions to decrease the viscosity, to decrease the set time or to increase the heat resistance of a hot melt composition. Because waxes are crystalline at room temperature, they tend to cause hot melt compositions formulated therewith to crystallize quickly from the molten stage, which can decrease the set time relative to the composition without the wax. Although this is desirable in some applications, in many applications decreasing the set time will decrease the utility of the hot melt adhesive composition.

Waxes generally are known to detackify pressure sensitive adhesive compositions. In hot melt pressure sensitive adhesive formulations, waxes tend to bloom to the surface of the hot melt composition, which detackifies the composition. For this reason, waxes often are not present in pressure sensitive adhesive formulations.

Wax also tends to crystallize while aging in an elevated temperature environment. When a hot melt adhesive composition is formulated with such a wax, this property tends to impair the ability of the composition to maintain a surface bond to a substrate when exposed to an elevated temperature for an extended period of time.

SUMMARY

In one aspect, the invention features a hot melt pressure-sensitive adhesive composition that includes a thermoplastic elastomer that includes a block copolymer that includes at least one A block that includes polyvinyl aromatic compound and at least one B block that includes an elastomeric conjugated diene (e.g., hydrogenated conjugated dienes, unhydrogenated conjugated dienes, and combinations thereof), tackifying agent, plasticizer oil, and from at least 5% by weight to about 25% by weight vegetable wax. In some embodiments, the thermoplastic elastomer includes at least one of styrene-isoprene-styrene, styrene-butadiene-styrene, styrene-ethylene-propylene-styrene, styrene-ethylene-butylene-styrene, and styrene-ethylene-ethylene-propylene-styrene. In other embodiments, the vegetable wax is derived from at least one of soy, palm, corn, and cottonseed. In another embodiment, the vegetable wax includes at least one triglyceride.

In some embodiments the composition includes from 5% by weight to about 20% by weight vegetable wax. In other embodiments the composition includes at least about 7% by weight vegetable wax. In another embodiment, the composition includes at least about 10% by weight vegetable wax.

In some embodiments, the composition further includes superabsorbent polymer.

In one embodiment, the composition further includes from about 1% by weight to about 60% by weight superabsorbent polymer.

In other embodiments, the composition exhibits a peel force of at least about 0.2 lb/linear inch. In some embodiments, the composition exhibits a peel force of at least about 2 lb/linear inch.

In one embodiment, the composition exhibits an onset of crystallization from melt of no greater than about 50° C. In other embodiments, the composition exhibits an onset of crystallization from melt of no greater than about 40° C.

In some embodiments, the composition includes from about 5% by weight to about 30% by weight elastomer, from about 10% by weight to about 60% by weight tackifying agent, from about 2% by weight to about 30% by weight plasticizer oil, and from about 7% by weight to about 20% by weight vegetable wax.

In one embodiment the vegetable wax is soy wax.

In another embodiment, the composition exhibits a T-Peel value after aging for two weeks at 120° F. that is greater than its initial T-Peel value.

In some embodiments, the pressure-sensitive adhesive composition further includes metallocene polymer. In other embodiments, the pressure-sensitive adhesive composition further includes at least 5% by weight metallocene polymer.

In another aspect, the invention features a hot melt pressure-sensitive adhesive composition that includes metallocene polymer, tackifying agent, plasticizer oil, and vegetable wax. In some embodiments the composition includes from about 5% by weight to about 30% by weight metallocene polymer, from about 10% by weight to about 60% by weight tackifying agent, from about 2% by weight to about 30% by weight plasticizer oil, and from about 3% by weight to about 25% by weight vegetable wax. In one embodiment the composition exhibits a T-Peel value after aging for two weeks at 120° F. that is greater than its initial T-Peel value. In other embodiments the composition exhibits a T-Peel value after aging for two weeks at 120° F. that is at least 25% greater than its initial T-Peel value.

In other aspects, the invention features a hot melt composition that includes from 5% by weight to about 70% by weight of a hot melt pressure sensitive adhesive composition disclosed herein and superabsorbent polymer.

In another aspect, the invention features an article that includes a substrate and a hot melt composition disclosed herein disposed on the substrate. In one embodiment, the article includes an absorbent article that includes an absorbent element, and a hot melt composition disclosed herein. In one embodiment, a disposable diaper, sanitary napkin, wound care product, wipe, towel or tissue includes an absorbent article disclosed herein.

The present invention features a hot melt pressure sensitive adhesive composition that includes vegetable wax and exhibits good peel adhesion. The hot melt pressure sensitive adhesive composition also exhibits good wet out, which assists in the formation of a good surface bond, and an onset of crystallization from melt at a temperature that is sufficiently low so as to permit a good mechanical bond to form between the composition and a substrate.

Other features and advantages will be apparent from the following description of the drawings and the preferred embodiments and from the claims.

GLOSSARY

In reference to the invention, these terms have the meanings set forth below:

The term "hot melt adhesive composition" means a solvent-free adhesive composition that is applied out of a molten state.

The term "hot melt pressure-sensitive adhesive composition" means a hot melt adhesive composition that retains surface tackiness over time including when cooled.

The term "pressure-sensitive adhesive" means an adhesive that is aggressively and permanently tacky at room temperature and firmly adheres to a variety of dissimilar surfaces upon mere contact without the need of more than finger or hand pressure.

DETAILED DESCRIPTION

The hot melt pressure sensitive adhesive composition includes vegetable wax, thermoplastic polymer, tackifying resin and plasticizer. The present inventors have discovered that the addition of a vegetable wax to a thermoplastic polymer-based hot melt pressure sensitive adhesive composition does not significantly detackify the hot melt pressure sensitive adhesive composition and does not significantly impair the peel adhesion properties of the composition. One measure of the degree of tack of a hot melt pressure sensitive adhesive composition is the 180° peel force exhibited by the composition. The hot melt pressure sensitive adhesive composition exhibits good peel adhesion, preferably a 180° peel force of at least about 0.2 lb/linear inch, at least about 2 lb/linear inch, or even at least about 4 lb/linear inch. The hot melt pressure sensitive adhesive composition preferably exhibits a greater 180° peel force relative to the same composition formulated with a paraffin wax.

The present inventors have further discovered that a hot melt pressure sensitive adhesive composition that includes vegetable wax can exhibit sufficient wet out to form a good surface bond and a sufficiently low onset of crystallization so as to enable the composition to form a good mechanical bond to a substrate, e.g., a porous substrate (e.g., a woven or a nonwoven web). The temperature at which the onset of crystallization occurs impacts the ability of a hot melt adhesive composition to form mechanical bond with a porous substrate. As a hot melt pressure sensitive adhesive crystallizes from melt, the ability of the adhesive to penetrate, flow into or interlock with a porous substrate decreases. Reducing the temperature at which an adhesive composition exhibits an onset of crystallization from melt increases the period of time during which the adhesive composition can form a bond with a substrate. The temperature at which the hot melt pressure sensitive adhesive composition exhibits an onset of crystallization is preferably no greater than about 50° C., no greater than 45° C., or even no greater than 40° C.

The hot melt pressure sensitive adhesive composition that includes vegetable wax also preferably exhibits a lower onset of crystallization relative to the same composition formulated with a paraffin wax.

The hot melt pressure sensitive adhesive composition also preferably exhibits a peak T-Peel value after aging for two weeks at 120° F. that is greater than the initial peak T-Peel value (i.e., the value obtained 24 hours after sample preparation), at least 25% greater than the initial peak T-Peel value, or even at least 50% greater than the initial peak T-Peel value.

The hot melt pressure sensitive adhesive composition can be formulated to exhibit a suitable viscosity. Useful hot melt pressure sensitive adhesive compositions exhibit a viscosity of no greater than 500,000 centipoises (cps) at 177° C., no greater than 100,000 cps at 177° C., or even no greater than 1000 cps at 177° C., or even from about 200 cps to about 20,000 cps at 135° C., or from about 200 cps to about 1000 cps at 135° C.

The vegetable wax of the hot melt pressure sensitive adhesive composition can be any suitable wax derived from at least one plant source including, e.g., soybean, cottonseed, corn, sunflower, canola, palm, coconut, rape, carambe, and linseed. Particularly useful waxes include waxes derived from hydrogenated oils of the aforementioned plant sources. Particularly useful waxes include waxes derived from hydrogenated oils of palm and soybean. The vegetable wax preferably is a high triglyceride wax having greater than 90% by weight triglyceride with trace amounts of fatty acids. Suitable waxes include 98% triglyceride by weight with trace amounts of fatty acids including, e.g., stearic acid, palmitic acid, myristic acid, and oleic acid and combinations thereof.

Useful vegetable waxes have a melting point from about 130° F. to about 180° F., and a mettler drop point of from about 120° F. to about 180° F. One example of a useful soybean oil wax has a melting point, as measured by the Mettler Drop Point, of from 155° F. to 160° F., another example of a useful soybean oil wax has a melting point, as measured by the Mettler Drop Point, of from about 125° F. to about 135° F., and one example of a useful palm oil wax has a melting point of from 136° F. to 142° F. The vegetable wax preferably has a viscosity from about 10 centipoise (cps) to about 200 cps at a temperature of 210° F., and an iodine value of from about 0 to about 30, from about 0 to about 10, or even from about 2 to about 5.

Useful waxes are commercially available from Archer Daniels Midland (ADM) (Decatur, Ill.) under the product number designation ADM Vegetable Wax Product Code 866970, from Cargill Incorporated (Wayzata, Minn.) under the product designation Stable Flake S, from Custom Shortenings & Oils (Richmond, Va.) under product designation Master Chef Stable Flake-P palm oil wax, and from Marcus Oil and Chemical Corp. (Houston, Tex.) under the product designations Marcus Nat 155, Marcus Nat 135, and Marcus Nat 125 for soybean waxes.

The vegetable wax is present in the adhesive compositions in an amount at least about 2% by weight, at least about 3% by weight, at least 5% by weight, at least about 7% by weight, at least about 10% by weight, from about 2% by weight to about 30% by weight, from 5% by weight to about 25% by weight, or even from about 10% to about 20% by weight.

The adhesive composition preferably includes thermoplastic polymer in an amount from about 5% by weight to about 35% by weight, from about 10% by weight to about 30% by weight, or even from about 15% by weight to about 25% by weight.

One class of thermoplastic polymers suitable for use in the hot melt adhesive composition is thermoplastic elastomers. Suitable thermoplastic elastomers include block copolymers having at least one A block that includes a vinyl aromatic compound and at least one B block that includes an elastomeric conjugated diene, including hydrogenated, unhydrogenated conjugated dienes, and combinations thereof. The A blocks and the B blocks may bind to one another in any manner of binding such that the resulting copolymer is random, block, straight-chained, branched, radial, or a combination thereof. The block copolymer can exhibit any form including, e.g., linear A-B block, linear A-B-A block, linear A-(B-A)$_n$-B multi-block, and radial (A-B)$_n$-Y block where Y is a multivalent compound and n is an integer of at least 3, tetrablock copolymer, e.g., A-B-A-B, and pentablock copolymers having a structure of A-B-A-B-A. The adhesive composition can include blends of at least two different block copolymers.

Useful vinyl aromatic compounds include, e.g., styrene, alpha-methylstyrene, o-methylstyrene, m-methylstyrene, p-methylstyrene, p-tert-butylstyrene, 2,4-dimethylstyrene, 2,4,6-trimethylstyrene, diphenylethylenes including stilbene, vinyl naphthalene, vinylanthracene, vinyltoluene (a mixture of meta- and para-isomers of methylstyrene), vinylxylene, and combinations thereof. Suitable conjugated dienes include, e.g., butadiene (e.g., polybutadiene), isoprene (e.g., polyisoprene), 2,3-dimethyl-1,3-butadiene, 1,3-pentadiene, 1,3-hexadiene, and combinations thereof, and hydrogenated versions thereof including, e.g., ethylene, propylene, butylene and combinations thereof.

Useful block copolymers include polyvinyl aromatic in an amount from about 0% by weight to about 50% by weight, from about 5% by weight to about 50% by weight, from about 15% by weight to 35% by weight, or even from about 20% by weight to about 30% by weight. Suitable block copolymers have a melt flow index of from about 3 g/10 min to about 50 g/10 min, or from about 5 g/10 min to about 20 g/10 min, as determined by ASTM-d 1238-95.

The A block can also include a small amount (e.g., no greater than 10% by weight based on the weight of the A block) of a structural unit derived from unsaturated monomers other than the vinyl aromatic compounds including, e.g., 1-butene, pentene, hexene, butadiene, isoprene, methyl vinyl ether, methyl methacrylate, vinyl acetate and combinations thereof. The B block can also include a small amount (e.g., no greater than 10% by weight based on the amount of the B block) of a structural unit derived from unsaturated monomers other than the conjugated diene including, e.g., 1-butene, 1-pentene, 1-hexene, methyl vinyl ether, styrene, methyl methacrylate, and combinations thereof.

Useful elastomeric polymers include, e.g., rubber (polyisoprene), polybutadiene, synthetic polyisoprene, random styrene-butadiene polymers, styrene-butadiene block copolymers, multiarmed and repeating styrene-butadiene copolymers, styrene-butadiene-styrene block copolymers, styrene-isoprene block copolymers, styrene-isoprene-styrene block copolymers, styrene-multiarmed styrene-isoprene (SI)$_x$ block copolymers, styrene-ethylene-butylene-styrene block copolymers, styrene-isobutylene-styrene block copolymers, styrene-ethylene-ethylene-propylene-styrene block copolymers, styrene-ethylene-propylene-styrene block copolymers and combinations thereof.

Useful block copolymers are commercially available under the KRATON D and G series of trade designations from Shell Chemical Company (Houston, Tex.) including, e.g., KRATON D 1163 and 1117 and KRATON G 1652 and 1726, EUROPRENE Sol T trade designation from EniChem (Houston, Tex.), SEPTON trade designation from Septon Company of America (Pasadena, Tex.) including SEPTON S 1001 styrene-ethylene-propylene-styrene block copolymer, and SEPTON 4030, 4033, 4044, 4055 and 4077 block copolymers, and VECTOR series of trade designations from Dexco (Houston, Tex.) including VECTOR 4211 styrene-isoprene-styrene block copolymer.

The elastomer is present in the adhesive composition in an amount from 0% by weight to about 35% by weight, from about 5% by weight to about 35% by weight, from about 10% by weight to about 30% by weight, or even from about 15% by weight to about 25% by weight.

Another class of thermoplastic polymers suitable for use in the hot melt adhesive composition is metallocene polymers. Metallocene polymers are prepared using a constrained geometry or single site metallocene catalyst. Useful metallocene polymers include, e.g., a homogeneous linear or substantially linear polymers that are interpolymers of ethylene and at least one $C_3$-$C_{20}$ α-olefin including e.g., ethylene/α-olefin/diene terpolymers. The term "homogenous" as used with respect to the metallocene polymer indicates that any comonomer is randomly distributed within a given interpolymer molecule and substantially all of the interpolymer molecules have the same ethylene/comonomer ratio within that interpolymer. Linear ethylene interpolymers are interpolymers that have an interpolymer backbone substituted with less than 0.01 long chain branches per 1000 carbons. The substantially linear ethylene interpolymers are interpolymers that include long chain branching. The long chain branches have the same comonomer distribution as the polymer backbone and can be as long as about the same length as the length of the polymer backbone. Suitable substantially linear ethylene interpolymers have a polymer backbone substituted with from about 0.1 to about 3 long chain branches per 1000 carbons.

Useful $C_3$-$C_{20}$ α-olefins used in the preparation of ethylene interpolymers include, e.g., propylene, isobutylene, 1-butene, 1-hexene, 4-methyl-1-pentene, 1-heptene, 1-octene, cyclopentene, cyclohexene, cyclooctene and combinations thereof. The dienes suitable as comonomers, particularly in the making of ethylene/α-olefin/diene terpolymers, are typically non-conjugated dienes having from 6 to 15 carbon atoms. Useful examples of suitable non-conjugated dienes include: (1) straight chain acyclic dienes including, e.g., 1,4-hexadiene, 1,5-heptadiene, and 1,6-octadiene; (2) branched chain acyclic dienes including, e.g., 5-methyl-1,4-hexadiene, 3,7-dimethyl-1,6-octadiene, and 3,7-dimethyl-1,7-octadiene, (3) single ring alicyclic dienes including, e.g., 4-vinylcyclohexene, 1-allyl-4-isopropylidene cyclohexane, 3-allylcyclopentene, 4-allylcyclohexene, and 1-isopropenyl-4-butenylcyclohexene; and (4) multi-ring alicyclic fused and bridged ring dienes including, e.g., dicyclopentadiene, and cycloalkylidene-substituted norbornenes including, e.g., 5-methylene-2-norbornene, 5-methylene-6-methyl-2-norbornene, 5-methylene-6,6-dimethyl-2-norbornene, 5-propenyl-2-norbornene, 5-(3-cyclopentenyl)-2-norbornene, 5-ethylidene-2-norbornene, and 5-cyclohexylidene-2-norbornene.

Useful homogenous linear or substantially linear ethylene polymers have a narrow molecular weight distribution ($M_w/M_n$) including, e.g., from 1.5 to 3.5, or even from 1.8 to 2.8. Additionally, the substantially linear ethylene polymers can have a melt flow ratio ($I_{10}/I_2$) that may be varied independently of the polydispersity index. In some embodiments, the homogenous linear or substantially linear ethylene polymer has a melt index ($I_2$ at 190° C.) from about 1 g/10 min to about 2000 g/10 min, from about 1 g/10 min to about 500 g/10 min or even from about 1 g/10 min to about 10 g/10 min.

The adhesive compositions can include a blend of metallocene polymers. Useful metallocene polymer blends have a density of less than 0.895 g/cm$^3$, less than 0.885 g/cm$^3$, or even less than 0.875 g/cm$^3$.

Examples of useful metallocene polymers are described in U.S. Pat. Nos. 5,324,800, 5,548,014, 5,530,054 and 6,207,748 and incorporated herein.

Useful metallocene polymers are commercially available under the AFFINITY series of trade designations including EG 8200 polyolefin plastomer from Dow Chemical Company (Midland, Mich.), and linear ethylene polymers are commercially available under the EXACT series of trade designations from ExxonMobil (Texas).

The metallocene polymer is preferably present in the hot melt adhesive composition in an amount from about 0% by weight to about 50% by weight, from about 5% by weight to about 35% by weight, from about 10% by weight to about 30% by weight, or even from about 15% by weight to about 25% by weight.

Useful tackifying agents include, e.g., natural and modified rosins such as gum rosin, wood rosin, tall oil rosin, distilled rosin, hydrogenated rosin, dimerized rosin and polymerized rosin; rosin esters such as glycerol and pentaerythritol esters of natural and modified rosins including, e.g., glycerol esters of pale, wood rosin, glycerol esters of hydrogenated rosin, glycerol esters of polymerized rosin, pentaerythritol esters of hydrogenated rosin and phenolic-modified pentaerythritol esters of rosin; phenolic modified terpene, alpha methyl styrene resins and hydrogenated derivatives thereof including, e.g., the resin product resulting from the condensation in an acidic medium of a bicyclic terpene and a phenol; aliphatic petroleum hydrocarbon resins having a Ball and Ring softening point of from about 70° C. to 135° C.; the latter resins resulting from the polymerization of monomers consisting primarily of olefins and diolefins; including hydrogenated aliphatic petroleum hydrocarbon resins; aromatic petroleum hydrocarbon resins, and mixed aromatic and aliphatic paraffin hydrocarbon resins and the hydrogenated derivatives thereof; aromatic modified alicyclic petroleum hydrocarbon resins and the hydrogenated derivatives thereof; alicyclic petroleum hydrocarbon resins and the hydrogenated derivatives thereof; low molecular weight polylactic acid; and combinations thereof.

Useful rosin-based tackifiers are sold under the trade designation AQUATAC, SYLVALITE, SYLVATAC and SYLVAGUM, and useful polyterpene or terpene resins are sold under the trade designation SYLVARES, including SYLVAREZ ZT5100, by Arizona Chemical (Jacksonville, Fla.). Useful aliphatic hydrocarbon resins tackifiers, such as resins resulting from the polymerization of monomers consisting of olefins and diolefins, are sold under the trade designation ESCOREZ, including ESCOREZ 5400, ESCOREZ 5600, ESCOREZ 5615 and ESCOREZ 5690 from Exxon Mobil Chemical Company (Houston, Tex.). Useful alicyclic petroleum hydrocarbon tackifying resins are sold under the trade designation EASTOTAC, including EASTOTAC H-100L from Eastman Chemical (Kingsport, Tenn.), and useful aromatic and aliphatic tackifying resins are sold under the trade designation WINGTACK, including WINGTACK 86 from Sartomer Company (Exton, Pa.).

The tackifying agent is present in the adhesive composition in an amount from about 10% by weight to about 60% by weight, from about 15% by weight to about 50% by weight, or even from about 20% by weight to about 40% by weight.

The adhesive compositions can optionally include at least one plasticizer. Any suitable plasticizer can be used in the compositions including, e.g., naphthenic oils, white mineral oils, phthalate and adipate esters, oligomers of polypropylene, polybutenes, polyisoprene, hydrogenated polyisoprene, polybutadiene, benzoate esters, and combinations thereof.

Useful commercially available plasticizers include plasticizers sold under the NYFLEX series of trade designations including NYFLEX 222B from Nynas Corporation (Houston, Tex.), KAYDOL OIL from Sonneborn (Tarrytown N.Y.) PARAPOL polybutene from Exxon Mobil Chemical Company (Houston, Tex.), OPPANOL polyisobutylene from BASF (Ludwigsjhafen, Germany), and BENZOFLEX 352 benzoate ester plasticizer from Velsicol Chemical Company (Chicago, Ill.).

The plasticizer is present in the adhesive composition in an amount from about 5% by weight to about 35% by weight, from about 10% by weight to about 30% by weight, or even from about 15% by weight to about 25% by weight.

The hot melt pressure sensitive adhesive composition can include other additives including, e.g., stabilizers, antioxidants, pigments, dyes, ultraviolet light absorbers, and combinations thereof. Useful antioxidants include high molecular weight hindered phenols and multifunctional phenols. Useful stabilizers include phosphites, such as tris-(p-nonylphenyl)-phosphite (TNPP) and bis(2,4-di-tert-butylphenyl)4,4'-diphenylene-diphosphonite and di-stearyl-3,3'-thiodipropionate (DSTDP). Useful antioxidants are commercially available under trade designation IRGANOX, including IRGANOX 1010, from Ciba (Terrytown, N.Y.), and under the trade designation BNX, including BXN 1010, from Mayzo, Inc. (Norcross, Ga.).

The hot melt pressure sensitive adhesive compositions disclosed herein can be blended with superabsorbent polymer to form a hot melt adhesive composition that exhibits some tack (including, e.g., pressure-sensitive adhesive tack) or is free of tack. The superabsorbent polymer can be in any suitable form including, e.g., particulate, fiber, flakes, and combinations thereof. Superabsorbent polymers are also referred to as water-insoluble absorbent hydrogel-forming polymers, "hydrogel-forming" polymers, and "hydrocolloids." Superabsorbent polymers are able to absorb many times their own weight in water. Useful superabsorbent polymers include at least partially crosslinked, at least partially neutralized polymers that gel when contacted with water and are preferably substantially water insoluble. Suitable superabsorbent polymers include, e.g., polysaccharides (e.g., carboxymethyl starch, carboxymethyl cellulose, and hydroxypropyl cellulose), polyvinyl alcohol, polyvinyl ethers, polyvinyl pyridine, polyvinyl morpholinione, N,N-dimethylaminoethyl, N,N-diethylaminopropyl, acrylates, methacrylates, and the quaternary salts thereof. The superabsorbent polymer preferably includes a plurality of functional groups, e.g., sulfonic acid groups, carboxy groups and combinations thereof.

Suitable superabsorbent polymers are prepared from polymerizable, unsaturated, acid-containing monomers including, e.g., olefinically unsaturated acids and anhydrides having at least one carbon-carbon olefinic double bond including, e.g., olefinically unsaturated carboxylic acids and acid anhydrides, olefinically unsaturated sulfonic acids and combinations thereof. Useful olefinically unsaturated carboxylic acid and carboxylic acid anhydride monomers include, e.g., acrylic acid, methacrylic acid, ethacrylic acid, chloroacrylic acid, cyanoacrylic acid, crotonic acid, phenylacrylic acid, acrytoxypropionic acid, sorbic acid, chlorosorbic acid, angelic acid, cinnamic acid, p-chlorocinnamic acid, stearylacrylic acid, itaconic acid, citraconic acid, mesaconic acid, glutaconic acid, aconitic acid, maleic acid, fumaric acid, tricarboxyethylene acid anhydride, maleic acid anhydride, and combinations thereof.

Useful olefinically unsaturated sulfonic acid monomers include aliphatic and aromatic vinyl sulfonic acids (e.g., vinylsulfonic acid, allyl sulfonic acid, vinyl toluene sulfonic acid and styrene sulfonic acid), acrylic and methacrylic sulfonic acids (e.g., sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid), and combinations thereof.

Useful superabsorbent polymers that include carboxy groups include, e.g., hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers are disclosed, e.g., in U.S. Pat. Nos. 4,076,663, 4,093,776, 4,666,983 and 4,734,478 and incorporated herein.

The absorbent gelling particles can have any suitable property including, e.g., size, shape, morphology and combinations thereof. The superabsorbent particles preferably are spherical or substantially spherical and preferably have an average particle size no greater than about 400 µm, no greater than about 350 µm, no greater than about 200 µm, no greater than about 150 µm, no greater than about 100 µm, no greater than about 100 µm, no greater than about 50 µm, no greater than about 40 µm, at least about 10 µm, at least about 20 µm, or even about 20 µm to about 30 µm. Suitable the spherical particle include those particles having surface imperfections.

Useful commercially available superabsorbent particles include, e.g., sodium polyacrylate superabsorbent particles available under the AQUA KEEP series of trade designations including, e.g., particles having a median particle size of from about 20 µm to about 30 µm available under the trade designation AQUA KEEP 10SH-NF, particles having an average particle size of from 200 µm to 300 µm available under the trade designation AQUA KEEP 10SH-P, particles having an average particle size of from 320 µm to 370 µm available under the trade designation AQUA KEEP SA60S, particles having an average particle size of from 350 µm to 390 µm available under the trade designations AQUA KEEP SA60SX, SA55SX II and SA60SL II, particles having an average particle size of from 250 µm to 350 µm available under the trade designation AQUA KEEP SA60N TYPE II from Sumitomo Seika Chemicals Col, Ltd. (Japan), powdered superabsorbent particles available under the AQUASORB series of trade designations including, e.g., AQUASORB A380 and AQUASORB A500 from Hercules Incorporated (Wilmington, Del.), and superabsorbent particles available under the LUQUASORB designations including, e.g., LUQUASORB 1010 and LUGUASORB 1003 from BASF (Florham Park, N.J.). Useful superabsorbent polymer forms include, e.g., particles, granules, flakes, pulveruients, interparticle aggregates, interparticle crosslinked aggregates, fibers, foams, and combinations thereof.

The hot melt superabsorbent polymer composition preferably includes superabsorbent polymer particles in an amount of at least about 30% by weight, at least about 40% by weight, at least about 50% by weight, no greater than about 70% by weight, or even no greater than about 60% by weight.

The hot melt superabsorbent polymer composition can also include other additives including, e.g., plasticizers, tackifying agents, waxes, antioxidants, biocides, chitosan, antimicrobial agents, scenting agents, antifungal agents, zeolites, carbon black, pigments, fillers (e.g., titanium dioxide and hydrophilic fillers), surfactants, phosphites (e.g., IRGAFOS 168), antiblock additives, and combinations thereof.

Useful hot melt superabsorbent polymer compositions are described in, e.g., U.S. Pat. Nos. 6,534,572, and 6,458,877, and U.S. patent application Ser. Nos. 10/050,375 (published as U.S. Publication No. 2003/0134552), and 11/007,470, and incorporated herein. Useful hot melt superabsorbent polymer compositions are commercially available under the HYDROLOCK series of trade designations from H.B. Fuller Company (Vadnais Heights, Minn.).

When present, the hot melt adhesive composition includes superabsorbent polymer in an amount from about 1% by weight to about 70% by weight, from about 5% by weight to about 60% by weight, or even from about 10% by weight to about 55% by weight.

The hot melt composition is useful in a variety of forms including, e.g., coating (e.g., continuous coatings and discontinuous (e.g., random, pattern, and array) coatings), film (e.g., continuous films and discontinuous films), binder, and fiber. The hot melt adhesive composition can be applied to or incorporated in a variety of substrates including, e.g., films (e.g., polyolefin (e.g., polyethylene and polypropylene) films), release liners, porous substrates, sheets (e.g., paper and fiber sheets), woven and nonwoven webs, and tape backings. The hot melt composition is also useful in a variety of applications including, e.g., packaging (e.g., boxes, cartons, and bags (e.g., paper and polymeric)), labels, disposable absorbent articles including, e.g., disposable diapers, feminine napkins, medical dressings (e.g., wound care products) wipes, tissues, towels (e.g., paper towels), sheets, mattress covers, and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue), and combinations thereof.

In one embodiment, the absorbent article includes a liquid pervious top sheet, a liquid impermeable backsheet, and the blend of hot melt pressure sensitive adhesive composition disclosed herein and superabsorbent polymer disposed between the top sheet and the backsheet.

Various application techniques can be used to apply the hot melt composition to a substrate including, e.g., slot coating, spraying including, e.g., spiral spraying and random spraying, screen printing, foaming, engraved roller, extrusion and meltblown adhesive application techniques.

The invention will now be described by way of the following examples. All parts, ratios, percents and amounts stated in the Examples are by weight unless otherwise specified.

EXAMPLES

Test Procedures

Test procedures used in the examples include the following.

180° Peel Force Test Method

180° Peel Force is determined as follows. Samples are prepared by coating the sample composition on to a Mylar polyester film at a coat weight of 25 g/m². The Mylar film is then cut into strips 1 inch wide by 8 inches long. Five inches of the adhesive coated side of the test specimen is applied to a stainless steel test panel without pressure. A 5 pound rubber coated roller is passed over the specimen at a rate of approximately 12 inches per minute once in each lengthwise direction ensuring that the sample is free of entrapped air bubbles.

The free end of the specimen is doubled back on itself at an angle of 180 degrees and clamped in the load cell of a tensile tester and the stainless steel panel is secured to the sled of the tester. The film is then peeled at a constant rate of 12+/−1 inch per minute. The average value of five samples is obtained and recorded.

Onset of Crystallization Test Method

Onset of crystallization from melt is measured according to the following thermal treatment of the adhesives. The composition is placed in a differential scanning calorimetry (DSC) instrument and is heated from room temperature (approximately 25° C.) to 120° C. at 40° C. per minute, the composition is then held for 5 minutes at 120° C. The composition is then cooled to −60° C. at a rate of 200° C. per minute and is held for 5 minutes at −60° C. The composition is then heated to 120° C. at a rate of 10° C. per minute, held for 5 minutes at 120° C. and then cooled from 120° C. to −60° C. at a rate of 10° C. per minute. The data obtained from the step of cooling from 120° C. to −60° C. at a rate of 10° C. per minute is reported.

T-Peel Test Method

The temperature of the melt tank, hose and application head of a hot melt applicator are set to 300° F., the adhesive is melted and at least 800 g of adhesive are flushed through the tank and hose. The pump is then turned on and a tared paper cup is used to catch the adhesive flow for one minute. The flow rate is 12 g/min+/−1 g. The laminating machine is threaded with a HTS-5 corona treated polyethylene film (Tredegar) and a spundbond polypropylene nonwoven web having a basis weight of 23.1 g/m² such that the adhesive will contact the corona treated side of the polyethylene film. The application nozzle is positioned such that the adhesive open time (i.e., the time between coating the adhesive composition on the first substrate and contacting the coated adhesive composition with a second substrate) is approximately 0.2 seconds. The spiral spray pattern is 0.5 inch wide and the pattern is such that the spirals just overlap. The standard coat weight is 0.004 g.

Test coupons, one inch wide by four inches long, are then cut from the laminate such that the coupons are 1 inch×4 inches, have a 1 inch square of paper at one end, and an adhesive bond running the length of the coupon.

After 24 hours the T-peels are run at 25° C. and 50% relative humidity. The calibration of the test machine is verified. The crosshead speed is set to 12 inches per minute and the dwell time is 10 seconds. The polyethylene film is placed in the stationary jaw of an Instron peel tester and the nonwoven web is placed in the moveable jaw. The peel is then started. The peak and average peel values of seven coupons are measured and recorded as initial T-peel. The failure mode is recorded. Seven samples are peeled. The remaining samples are placed in an oven at 120° F. 50% humidity for one week and four weeks. The average and peak peel values and standard deviation of seven coupons are measured and reported.

Viscosity

The viscosity of a sample is determined using a Brookfield Laboratories DVII+ Viscometer. The spindle used is a SC-27 hot-melt spindle suitable for measuring viscosities in the range of from 10 centipoise to 100,000 centipoise. The sample is placed in the in a disposable aluminum sample chamber, which in turn is inserted in to a Brookfield Thermosel and locked into place. The sample is heated to 275° F. (135° C.), with additional sample being added until the melted sample is about 1 inch (2.5 cm) below the top of the sample chamber. The viscometer apparatus is lowered and the spindle is submerged into the sample. The viscometer is turned on and set to a shear rate that leads to a torque reading in the range of from 30% to 60%. Readings are taken every minute for about 15 minutes or until the values stabilize. The final reading is recorded in centipoises (cps).

Water Absorption

Total water absorption is determined by drawing-down a molten film or heat-pressing a hot melt composition into a film having a thickness of 20 mils or a coating weight of approximately 0.3 g/in². The film is then cut into a 1 inch (2.54 cm) square and weighed. The sample film is then placed in a 50 ml cup and 30 ml of water (or more if needed) is poured on top of the film. After 30 minutes the unabsorbed water is filtered off and weighed. The total amount of water absorbed is determined and the milliliters (ml) of water absorbed per gram of composition is recorded as ml water/g composite.

0.9% Aqueous Saline Solution Absorption

Total 0.9% saline solution absorption is determined by drawing-down a molten film or heat-pressing the hot melt composition into a film having a thickness of 20 mils or a coating weight of approximately 0.3 g/in². The film is then cut into a 1 inch (2.54 cm) square and weighed. The sample film is then placed in a 50 ml cup and 30 ml (or more if needed) of 0.9% aqueous saline solution is poured on top of the film. After 30 minutes the unabsorbed saline solution is filtered off and weighed. The total amount of 0.9% aqueous saline solution absorbed is determined and the milliliters (ml) of 0.9% aqueous saline solution absorbed per gram of composition is recorded as ml 0.9% aqueous saline solution/g composite.

Iodine Value

Iodine value is determined according to ASTM test method D1959-97.

Control 1

Into a sigma blade mixer having a nitrogen atmosphere and heated to a temperature of 350° F. is added about 29.4 parts WINGTACK 86 tackifying resin (Sartomer, Exton, Pa.) and 19.3 parts SYLVAREZ ZT5100 tackifying resin (Arizona Chemical, Savannah, Ga.) and 0.3 parts IRGANOX 1010 antioxidant (Ciba Chemicals, N.Y.). The mixer is operated until the antioxidant is fully blended with the molten tackifying resin. Into the tackifying resin is added 14.7 parts of VECTOR 4211 styrene-isoprene-styrene block copolymer (Dexco, Huston, Tex.). After the copolymer has been fully added to the resin and a uniform melt is formed, 14.7 parts PACEMAKER 155 paraffin wax having a melting point of 67.98° C. (Citgo Chemical Company, Rolling Meadows, Ill.), and 19.6 parts NYFLEX 222B oil (Nynex Corporation, Sweden) are added to the melt. The sigma blade mixer is operated until the contents form a smooth melt blend and the material is withdrawn and packaged.

Example 1

A hot melt pressure sensitive adhesive composition is prepared as follows. Into a sigma blade mixer having a nitrogen atmosphere and heated to a temperature of 350° F. is added about 29.4 parts WINGTACK 86 tackifying resin and 19.3 parts SYLVAREZ ZT5100 tackifying resin (Arizona Chemical, Savannah, Ga.) and 0.3 parts IRGANOX 1010 antioxidant (Ciba Chemicals, N.Y.). The mixer is operated until the antioxidant is fully blended with the molten tackifying resin. Into the tackifying resin is added 14.7 parts of VECTOR 4211 styrene-isoprene-styrene block copolymer (Dexco, Houston, Tex.). After the copolymer has been fully added to the resin and a uniform melt is formed, 14.7 parts VEGETABLE WAX 866970 hydrogenated soybean oil wax having melting points at 64.3° C. and 55.8° C. (ADM, Decatur, Ill.), and 19.6 parts NYFLEX 222B oil (Nynex Corporation, Sweden) are added to the melt. The sigma blade mixer is operated until the contents form a smooth melt blend and the material is withdrawn and packaged.

Control 2

The hot melt pressure sensitive adhesive composition of Control 2 is prepared according to the procedure of Control 1 with the exception that the components present in the composition and the amounts thereof are as follows: 48.7% by weight ESCOREZ 5690 tackifying resin (ExxonMobil), 20.6% by weight NYFLEX 222B viscosity modifier, 13.7% by weight VECTOR 6241 sytene-butadiene-styrene block copolymer (ExxonMobil), 14.7% PACEMAKER 155 paraffin wax (Citgo Chemical Company), and 0.3% IRGANOX 1010 antioxidant.

Example 2

The hot melt pressure sensitive adhesive composition of Example 2 is prepared according to the procedure of Example 1 with the exception that the components present in the composition and the amounts thereof are as follows: 48.7% by weight ESCOREZ 5690 tackifying resin (ExxonMobil, Houston, Tex.), 20.6% by weight NYFLEX 222B viscosity modifier, 13.7% by weight VECTOR 6241 styrene-butadiene-styrene block copolymer (ExxonMobil), 14.7% VEGETABLE WAX 866970 hydrogenated soybean oil wax, and 0.3% IRGANOX 1010 antioxidant. A differential scanning calorimetry scan of the hot melt pressure sensitive adhesive composition of Example 2 is shown in FIG. 3. The G'/G" crossover point occurred at 48.425° C. and $2.965 \times 10^4$ dyn/$cm^2$. The right vertical axis is dyn/$cm^2$, the left vertical axis is tan delta and the horizontal axis is in degrees Celsius.

When Controls 1 and 2 and Examples 1 and 2 are tested according to the above-described viscosity, 180° Peel Force and Onset of Crystallization from Melt test methods the expected results are as set forth in Table 1.

TABLE 1

| Example | Viscosity (cps) at 275° F. | 180° Peel Force (lb/in) | Onset of Crystallization from Melt (° C.) |
|---|---|---|---|
| Control 1 | 630 | 1.8 | 60.5 |
| Example 1 | 635 | 2.6 | 36.9 |
| Control 2 | 575 | 0.5 | 59 |
| Example 2 | 560 | 1.8 | 36.3 |

Example 3

A superabsorbent hot melt adhesive composition was prepared by combining 47.98% by weight of the hot melt pressure sensitive adhesive composition of Example 2, 50% by weight AQUAKEEP 10SH-NF superabsorbent polymer (Sumitomo Chemical Company, Japan), 2.0% by weight RHODACAL DS10 surfactant (Rhodia, Cranberry, N.J.) and 0.02% SUDAN BLUE dye. The hot melt composition is expected to be tacky to the touch. The hot melt composition of Example 3 is expected to absorb 127 milliliters of distilled water per gram of composition and 30.7 milliliters of 0.9% saline solution per gram of composition.

Example 4

The hot melt composition of Example 4 is prepared according to the procedure of Example 1 with the exception that the components present in the composition and the amounts thereof are as follows: 14.0% by weight AFFINITY EG 8200 metallocene interpolymer (Dow Chemical Co., Midland, Mich.), 52.3% by weight PICCOTAC 8095 tackifying resin (Eastman Chemical Company), 26.5% by weight NYFLEX 222B viscosity modifier, 5% by weight STABLE FLAKES S soy vegetable wax, 0.2% by weight BXN 1010 antioxidant, and 0.25% by weight ZP FILM processing aid.

Example 4, when tested according to the above-described T-Peel test method, is expected to exhibit the results set forth in Table 2.

TABLE 2

| Time after Sample Preparation | Peak T-Peel (g) |
|---|---|
| 24 hours | 146 |
| 2 weeks at 120° F. | 226 |

Example 5

The hot melt pressure sensitive adhesive composition of Example 5 is prepared according to the procedure of Example 1 with the exception that the components present in the composition and the amounts thereof are as follows: 15% by weight VECTOR 4114 styrene-isoprene-styrene block copolymer (ExxonMobil, Houston, Tex.), 45.0% by weight ESCOREZ 5400 hydrogenated tackifying resin (ExxonMobil), 19.7% by weight NYFLEX 222B oil, 20.0% by weight VEGETABLE WAX 866970 hydrogenated soybean oil wax (ADM), and 0.3% IRGANOX 1010 antioxidant.

Example 6

The hot melt pressure sensitive adhesive composition of Example 6 is prepared according to the procedure of Example 1 with the exception that the components present in the composition and the amounts thereof are as follows: 5% by weight KRATON G 1657 styrene-ethylene-butylene-styrene block copolymer (Kraton, Polymers LLC, Houston, Tex.), 15.0% by weight AFFINITY EG 8200 ethylene alpha olefin interpolymer (Dow Chemical Company, Midland, Mich.), 45.0% by weight ESCOREZ 5400 hydrogenated tackifying resin (ExxonMobil), 24.7% by weight NYFLEX 222B oil, 10.0% by weight VEGETABLE WAX 866970 hydrogenated soybean oil wax (ADM), and 0.3% IRGANOX 1010 antioxidant.

Example 7

The hot melt pressure sensitive adhesive composition of Example 7 is prepared according to the procedure of Example 6 with the exception that the components present in the composition and the amounts thereof are as follows: 10% by weight KRATON G 1657 styrene-ethylene-butylene-styrene block copolymer (Kraton, Polymers LLC), 10.0% by weight AFFINITY EG 8200 ethylene alpha olefin interpolymer (Dow Chemical Company), 40.0% by weight ESCOREZ 5400 hydrogenated tackifying resin (ExxonMobil), 19.7% by weight NYFLEX 222B oil, 20.0% by weight VEGETABLE WAX 866970 hydrogenated soybean oil wax (ADM), and 0.3% IRGANOX 1010 antioxidant.

Example 8

The hot melt pressure sensitive adhesive composition of Example 8 is prepared according to the procedure set forth in Example 1 with the exception that the components present in the composition and the amounts thereof are as follows: 20% by weight VECTOR 4114 styrene-isoprene-styrene block copolymer (ExxonMobil), 40.0% by weight WINGTACK 86 tackifying resin (ExxonMobil), 19.7% by weight NYFLEX 222B oil, 20.0% by weight VEGETABLE WAX 866970 hydrogenated soybean oil wax (ADM), and 0.3% IRGANOX 1010 antioxidant.

When Examples 5-8 are tested according to the above-described viscosity and 180° Peel Force test methods the expected results are as set forth in Table 3.

TABLE 3

| Example | Viscosity (cps) at 275° F. | 180° Peel Force (lb/in) | On set of Crystallization from Melt (° C.) |
|---|---|---|---|
| Example 5 | 890 | 1.8 | 38.8 |
| Example 6 | 16,100 | 0.5 | 31.83 |
| Example 7 | 10,020 | 0.2 | 37.19 |
| Example 8 | 1450 | 2.0 | 39.88 |

Other embodiments are within the claims.

All of the patents and patent applications cited above are incorporated by reference into this document in total.

What is claimed is:

1. A hot melt pressure-sensitive adhesive composition comprising:
   a thermoplastic elastomer comprising a block copolymer comprising at least one A block comprising polyvinyl aromatic compound and at least one B block comprising an elastomeric unhydrogenated conjugated diene, hydrogenated conjugated diene or a combination thereof;
   tackifying agent;
   plasticizer oil; and
   from at least 5% by weight to about 25% by weight vegetable wax the pressure-sensitive adhesive composition exhibiting an onset of crystallization from melt of no greater than about 50° C.

2. The hot melt pressure-sensitive adhesive composition of claim 1, wherein said thermoplastic elastomer comprises at least one of styrene-isoprene-styrene, styrene-butadiene-styrene, styrene-ethylene-propylene-styrene, and styrene-ethylene-butylene-styrene, and styrene-ethylene-ethylene-propylene-styrene.

3. The pressure-sensitive adhesive composition of claim 1, wherein said vegetable wax is derived from at least one of soy, palm, corn, and cottonseed.

4. The pressure-sensitive adhesive composition of claim 1, wherein said vegetable wax comprises at least one triglyceride.

5. The pressure-sensitive adhesive composition of claim 1, comprising from 5% by weight to about 20% by weight vegetable wax.

6. The pressure-sensitive adhesive composition of claim 1, comprising from at least about 7% to about 25% by weight vegetable wax.

7. The pressure-sensitive adhesive composition of claim 1, comprising from at least about 10% to about 25% by weight vegetable wax.

8. The pressure-sensitive adhesive composition of claim 1, further comprising superabsorbent polymer.

9. The pressure-sensitive adhesive composition of claim 1, further comprising from about 1% by weight to about 60% by weight superabsorbent polymer.

10. The pressure-sensitive adhesive composition of claim 1, exhibiting a peel force of at least about 0.2 lb/linear inch.

11. The pressure-sensitive adhesive composition of claim 1, exhibiting a peel force of at least about 2 lb/linear inch.

12. The pressure-sensitive adhesive composition of claim 1, exhibiting an onset of crystallization from melt of no greater than about 40° C.

13. The pressure-sensitive adhesive composition of claim 1, comprising
   from about 5% by weight to about 30% by weight said elastomer;
   from about 10% by weight to about 60% by weight said tackifying agent;
   from about 2% by weight to about 30% by weight plasticizer oil; and
   from about 7% by weight to about 20% by weight said vegetable wax.

14. The pressure-sensitive adhesive composition of claim 1 further comprising metallocene polymer.

15. The pressure-sensitive adhesive composition of claim 1 further comprising at least 5% by weight metallocene polymer.

16. The pressure-sensitive adhesive composition of claim 1, wherein said vegetable wax is soy wax.

17. The pressure-sensitive adhesive composition of claim 1 exhibiting a T-Peel value after aging for two weeks at 120° F. that is greater than its initial T-Peel value.

18. A hot melt composition comprising:
   from 5% by weight to about 70% by weight of the hot melt pressure sensitive adhesive composition of claim 1; and
   superabsorbent polymer.

19. A hot melt pressure-sensitive adhesive composition comprising:
   a metallocene polymer;
   tackifying agent;
   plasticizer oil; and
   vegetable wax the pressure-sensitive adhesive composition exhibiting an onset of crystallization from melt of no greater than about 50° C.

20. The pressure-sensitive adhesive composition of claim 19, comprising
   from about 5% by weight to about 30% by weight said metallocene polymer;
   from about 10% by weight to about 60% by weight said tackifying agent;
   from about 2% by weight to about 30% by weight plasticizer oil; and
   from about 3% by weight to about 25% by weight said vegetable wax.

21. The pressure-sensitive adhesive composition of claim 19 exhibiting a T-Peel value after aging for two weeks at 120° F. that is greater than its initial T-Peel value.

22. The pressure-sensitive adhesive composition of claim 19 exhibiting a T-Peel value after aging for two weeks at 120° F. that is at least 25% greater than its initial T-Peel value.

23. An article comprising:
   a substrate; and
   a hot melt pressure sensitive adhesive composition disposed on said substrate, said hot melt pressure sensitive adhesive composition comprising the composition of claim 19.

24. An article comprising:
   a substrate; and
   a pressure sensitive adhesive composition disposed on said substrate, said pressure sensitive adhesive composition comprising the composition of claim 1.

25. A disposable diaper, sanitary napkin, wound care product, wipe, towel or tissue comprising the article of claim 24.

26. A hot melt pressure-sensitive adhesive composition comprising:
a thermoplastic elastomer comprising a block copolymer comprising at least one A block comprising polyvinyl aromatic compound and at least one B block comprising an elastomeric unhydrogenated conjugated diene, hydrogenated conjugated diene or a combination thereof;
tackifying agent;
plasticizer oil; and
from at least 5% by wax,
the pressure-sensitive adhesive composition exhibiting a peel force of at least about 0.2 lb/linear inch.

27. A hot melt pressure-sensitive adhesive composition comprising:
a thermoplastic elastomer comprising a block copolymer comprising at least one A block comprising polyvinyl aromatic compound and at least one B block comprising an elastomeric unhydrogenated conjugated diene, hydrogenated conjugated diene or a combination thereof;
tackifying agent;
plasticizer oil; and
from at least 5% by weight to about 25% by weight vegetable wax,
the pressure-sensitive adhesive composition exhibiting a peel force of at least about 2 lb/linear inch.

28. A hot melt pressure-sensitive adhesive composition comprising:
a thermoplastic elastomer comprising a block copolymer comprising at least one A block comprising polyvinyl aromatic compound and at least one B block comprising an elastomeric unhydrogenated conjugated diene, hydrogenated conjugated diene or a combination thereof;
tackifying agent;
plasticizer oil; and
from at least 5% by weight to about 25% by weight vegetable wax,
the pressure-sensitive adhesive composition exhibiting a T-Peel value after aging for two weeks at 120° F. that is greater than its initial T-Peel value.

29. A hot melt pressure-sensitive adhesive composition comprising:
a metallocene polymer;
tackifying agent;
plasticizer oil; and
vegetable wax,
the composition exhibiting a T-Peel value after aging for two weeks at 120° F. that is greater than its initial T-Peel value.

30. A hot melt pressure-sensitive adhesive composition comprising:
a metallocene polymer;
tackifying agent;
plasticizer oil; and
vegetable wax,
the composition exhibiting a T-Peel value after aging for two weeks at 120° F. that is at least 25% greater than its initial T-Peel value.

* * * * *